(12) United States Patent
Liu

(10) Patent No.: US 10,463,379 B2
(45) Date of Patent: Nov. 5, 2019

(54) CUSTOMIZED SURGICAL CUTTING GUIDE FOR TOTAL KNEE REPLACEMENT AND METHOD FOR MAKING THEREOF

(71) Applicant: Shanghai Xinjian Medical Co., LTD., Shanghai (CN)

(72) Inventor: Fei Liu, Shanghai (CN)

(73) Assignee: SHANGHAI XINJIAN MEDICAL CO., LTD., Shanghai (CN)

( * ) Notice: Subject to any disclaimer, the term of this patent is extended or adjusted under 35 U.S.C. 154(b) by 393 days.

(21) Appl. No.: 15/370,951

(22) Filed: Dec. 6, 2016

(65) Prior Publication Data
US 2017/0156741 A1 Jun. 8, 2017

(30) Foreign Application Priority Data
Dec. 7, 2015 (CN) .......................... 2015 1 0883484

(51) Int. Cl.
| | |
|---|---|
| A61B 17/15 | (2006.01) |
| A61B 17/17 | (2006.01) |
| B33Y 80/00 | (2015.01) |
| B29C 64/386 | (2017.01) |
| A61B 17/00 | (2006.01) |
| A61B 34/10 | (2016.01) |

(52) U.S. Cl.
CPC ........ *A61B 17/155* (2013.01); *A61B 17/1764* (2013.01); *B29C 64/386* (2017.08); *B33Y 80/00* (2014.12); *A61B 2017/00526* (2013.01); *A61B 2034/108* (2016.02)

(58) Field of Classification Search
CPC ...... A61B 17/15; A61B 17/154; A61B 17/155
See application file for complete search history.

(56) References Cited

U.S. PATENT DOCUMENTS

| | | | |
|---|---|---|---|
| 5,053,037 A | 10/1991 | Lackey | |
| 5,879,393 A | 3/1999 | Whiteside et al. | |
| 6,187,010 B1 | 2/2001 | Masini | |
| 6,575,980 B1 | 6/2003 | Robie et al. | |
| RE39,301 E | 9/2006 | Bertin | |
| 7,172,597 B2 | 2/2007 | Sanford | |
| 9,968,376 B2 * | 5/2018 | Metzger | .......... A61B 17/58 |
| 2010/0023015 A1 * | 1/2010 | Park | .......... A61B 17/15 606/87 |
| 2010/0191244 A1 * | 7/2010 | White | .......... A61B 17/155 606/88 |
| 2011/0071533 A1 * | 3/2011 | Metzger | .......... A61B 17/157 606/88 |

(Continued)

*Primary Examiner* — Eric S Gibson
(74) *Attorney, Agent, or Firm* — Cheng-Ju Chiang

(57) ABSTRACT

A customized surgical cutting guide mounted on a femur for TKR comprises a base having a plurality of cylinders located thereon, a pair of arms branching from a top of the base and each having a column located at a tip thereof, and a convex portion protruding from a bottom of the base and abutting against a corresponding portion of the femur. And wherein each cylinder has a through hole extending therethrough for allowing a kirschner pin to pass through, and wherein each column abuts against a corresponding portion of the femur and has a mounting hole extending therethrough for positioning the arms onto the corresponding positions of the femur, and wherein the arms, the cylinders, and the convex portion are located at the same side of the base.

20 Claims, 11 Drawing Sheets

(56) References Cited

U.S. PATENT DOCUMENTS

| | | | |
|---|---|---|---|
| 2011/0218545 A1* | 9/2011 | Catanzarite | A61B 17/155 606/96 |
| 2012/0143198 A1* | 6/2012 | Boyer | A61B 17/151 606/87 |
| 2012/0277751 A1* | 11/2012 | Catanzarite | A61B 17/155 606/88 |
| 2012/0316564 A1* | 12/2012 | Serbousek | A61B 17/1764 606/80 |
| 2012/0323244 A1* | 12/2012 | Cheal | A61B 17/155 606/87 |
| 2013/0006250 A1* | 1/2013 | Metzger | A61B 17/155 606/87 |
| 2013/0197528 A1* | 8/2013 | Zakaria | A61B 17/155 606/88 |
| 2013/0317510 A1* | 11/2013 | Couture | A61B 17/154 606/88 |
| 2014/0018813 A1* | 1/2014 | McKinnon | A61B 17/155 606/88 |
| 2014/0094814 A1* | 4/2014 | Hughes | A61B 17/155 606/88 |
| 2014/0142580 A1* | 5/2014 | Aram | A61B 17/155 606/89 |
| 2015/0142000 A1* | 5/2015 | Seedhom | A61B 17/15 606/87 |
| 2015/0182238 A1* | 7/2015 | Salehi | A61B 17/155 606/88 |
| 2015/0245879 A1* | 9/2015 | Nikou | A61B 17/1764 606/88 |
| 2016/0089153 A1* | 3/2016 | Couture | A61B 17/155 606/88 |
| 2016/0174994 A1* | 6/2016 | Hafez | A61B 17/155 606/88 |
| 2016/0367264 A1* | 12/2016 | Geebelen | A61B 17/155 |
| 2017/0156741 A1* | 6/2017 | Liu | A61B 17/1764 |
| 2017/0273718 A1* | 9/2017 | Metzger | A61B 17/58 |
| 2018/0116804 A1* | 5/2018 | Hafez | A61B 17/155 |
| 2018/0177512 A1* | 6/2018 | Hogan | A61B 17/155 |
| 2018/0185033 A1* | 7/2018 | Fritzinger | A61B 17/157 |
| 2018/0185097 A1* | 7/2018 | Langhorn | A61B 34/10 |
| 2018/0206888 A1* | 7/2018 | Metzger | A61B 17/58 |
| 2018/0235641 A1* | 8/2018 | McAuliffe | A61B 34/10 |
| 2018/0344335 A1* | 12/2018 | McKinnon | A61B 17/1764 |

* cited by examiner

CUSTOMIZED SURGICAL CUTTING GUIDE FOR TOTAL KNEE REPLACEMENT AND METHOD FOR MAKING THEREOF

BACKGROUND OF THE INVENTION

1. Field of the Invention

The present invention relates to a surgical instrument, more particularly to a customized surgical cutting guide used for surgical implantation of prosthetic knee component in total knee replacement (TKR) surgery and a method for making the customized surgical cutting guide.

2. Description of the Prior Art

In preparing the knee for implantation of a prosthesis in total knee replacement (TKR) surgery, there are basically three bony areas of the knee requiring resurfacing, namely the distal femur, proximal tibia, and the patella. Patella resurfacing is a relatively easy procedure and is achieved in essentially one step. Preparation of the femoral and tibial areas of the knee, however, is typically more complicated, requiring multiple cuts on the bone in precise locations thereon.

In many instances, a specially designed jig or fixture enables the surgeon to make accurate and precise bone resections of the femoral or tibial surface in order to accept the prosthesis. The ultimate goal with any total knee prosthesis is to approximate the function of the natural, healthy structure which is replaced by the prosthesis. However, any misalignment caused by attaching the prosthesis to an improper position of the femur could result in discomfort to the patient, or degradation of the prosthesis.

For example, when attached to a knee, the prosthesis is desirable to be oriented to a position where the pivot axis of the knee joint lies within a transverse plane which is perpendicular to the mechanical axis of the femur. The mechanical axis lies along a line which intersects the femoral head and the center of the ankle. In the prior art, the mechanical axis hand been determined from an inspection of a radiograph of the femur be resected prior to, or even during the surgery. During the actual operation, the mechanical axis is determined by computing its valgus angle from the femoral shaft axis. Then a cutting guide is manually aligned and fixed with respect to the femoral shaft axis to achieve an optimum cut.

The cutting guide used in TKR include includes a femoral intramedullary stem which is inserted through a pre-drilled passageway formed in the intercondylar notch and extending upwardly through the femur along the femoral shaft axis. The distal femur cutting guide often includes a bracket which supports the femoral intramedullary stem. The cutting guide includes pairs of opposing slots formed along the sides thereof. The slots are oriented to be perpendicular to a central axis of symmetry of the cutting guide. The bracket includes a first pin which extends through the cutting guide to act as a pivot axis. A second pin is attached to the bracket so as to extend through an arcuate slot in the cutting guide. An appropriate angle with the femoral shaft axis is defined by the central axis of the cutting guide lying along the mechanical axis and the slots are positioned to be perpendicular to the mechanical axis during the cutting guide being pivoted. Such that the cutting guide is locked into the predetermined angle with the femoral shaft axis, and resection of the distal femur may proceed.

Many examples of devices and methods may be found in the art for preparing the distal femur for total knee arthroplasty, such as U.S. Pat. No. 7,172,597 which discloses a provisional component for using with differently sized first and second prosthetic orthopedic components. The provisional component has a configuration that is substantially similar to the first prosthetic component and predefined correspondence to the second prosthetic component. The provisional component is mounted on a bone to assess the fit of the first prosthetic component. The provisional component includes a referencing element for defining a reference point on the bone if the fit of the provisional component indicates that the second prosthetic component should be used. An instrument guide is aligned with the reference point and used to properly position a surgical instrument for preparing the bone to receive the second prosthetic component. The provisional and prosthetic components may all be femoral components which have an articulating surface defining a single condylar-shaped projection.

U.S. Pat. No. RE39,301, incorporated herein by reference, discloses a method and apparatus for knee replacement surgery in which a femoral provisional component corresponding to a permanent component is provided to be implanted in a human. The provisional component is suitable for establishing a correct fit and position prior to the implantation thereof. The provisional component further includes a cutting guide for anterior surface resection such that accurate cuts may be made with the provisional component in place. The method involves preparing the distal femoral surface using the femoral intramedullary canal as a constant reference point for posterior and distal cutting guides, and then locating the provisional component by means of a provisional intramedullary stem, the relationship with the soft tissues of the knee may be accurately established.

U.S. Pat. No. 6,187,010, incorporated herein by reference, discloses bone cutting guides that appear to enable a surgeon to preferably gauge required resection characteristics. At least a portion of the guide is transparent to enable the user to optimize cut estimates and to visualize the resection. At least a portion of the outer surface of the guide-body is shaped to interact with another bone or prosthetic element associated with a joint, so as to enable the device to function both as a trial and as a cutting guide.

U.S. Pat. No. 5,879,393 discloses a posterior stabilized femoral trial apparatus for preparing a patient's femur to receive a posterior stabilized femoral prosthesis. The device includes a trial body with proximal and distal portions. The distal portion has an articulating surface for articulating with a patient's tibial component. A module selected from a kit fits the trial body at the proximal surface. The module includes a rasping surface that extends longitudinally. The trial body includes cutting surfaces at the posterior condyles. The module is removably attachable to the trial body at the proximal surface. The surgeon may resect the patient's femur in a revision case using the trial.

U.S. Pat. No. 6,575,980 discloses an instrument for shaping a femur preparatory to implantation of a knee prosthesis. A gap checking device is fixed to the distal end of the patient's femur and referenced to the epicondyles of the femur. The gap checking device includes slots through which a cutting instrument can be passed to shape the femur for receiving the femoral component of the prosthesis. One of the slots enables the distal femoral cut to be made. The thickness of the gap checking device is selected so that the distance between the distal femoral cut and the distal surface of the gap checking device plus the thickness of a shim resting on the cut proximal tibia surface is equal to the combined thickness of the tibial and femoral components of the prosthesis. This arrangement apparently enables balancing of the ligaments to be checked before the femoral cuts are made, but while the gap checking device is secured to the femur.

U.S. Pat. No. 5,053,037 discloses femoral instrumentation for long stem surgery, and provides a femoral drill guide with interchangeable femoral collets, a femoral reamer, and a femoral anterior/posterior cutting block with an adaptable anterior femoral ledge. This instrumentation allows all cuts to be made relative to the long stem component of a femoral prosthesis which will fit in the hole formed by the reamer with the collet and cutting block both oriented on the reamer, and all cuts made by the surgeon will be oriented relative to the long stem or spike component of the femoral prosthesis.

With many of the foregoing, except U.S. Pat. No. 6,187,010, it would be common practice to make one or more cuts with a resection guide in place, then moving the guide aside in order to view the interface to ensure that sufficient bone has been removed to facilitate the most ideal cement interface between the resected bone and implant component. This trial-and-error process not only consumes valuable time during the operation, but may lead to the removal of more bone stock than necessary to achieve fixation. During revision arthroplasty, such trial-and-error is complicated owing to the increased number of resected surfaces involved, and the need to ensure that these surfaces and the medullary stem are all properly aligned during the testing of trial implants and the attachment of the final prosthetic device. In the event of a misalignment, the surgeon may choose to use a final implant having a smaller than optimal diameter stem, for example, to take up the slack upon discovering a slight misalignment with respect to the stem and the resected surfaces. As such, none of the forgoing methods or devices have adequately provided surgeons with a way to easily locate resection guides in relation to the patient's body during orthopedic procedures, such as, total knee replacement surgery.

Accordingly, a customized surgical cutting guide used for surgical implantation of prosthetic knee component in total knee replacement (TKR) surgery and a method for making thereof that solves the above problems is desirable.

SUMMARY OF THE INVENTION

In accordance with the present invention, a customized surgical cutting guide used for surgical implantation of prosthetic knee component in TKR is provide to be rapidly and steadily attached to a distal end of a femur for guiding a surgical saw to achieve precise osteotomy, so as to avoid errors during bone cut caused by misalignment of the cutting guide.

In order to achieve the object set forth, a customized surgical cutting guide mounted on a femur for TKR comprises a base having a plurality of cylinders located thereon, a pair of arms branching from a top of the base and each having a column located at a tip thereof, and a convex portion protruding from a bottom of the base and abutting against a corresponding portion of the femur. And wherein each cylinder has a through hole extending therethrough for allowing a kirschner pin to pass through, and wherein each column abuts against a corresponding portion of the femur and has a mounting hole extending therethrough for positioning the arms onto the corresponding positions of the femur, and wherein the arms, the cylinders, and the convex portion are located at the same side of the base.

In order to achieve the object set forth, a method for making the customized surgical cutting guide described above comprises the follow steps: scanning an interest portion of the patient through a scanner to obtain the initial data of the interest portion; reconstructing the initial data to obtain a medical image of the interest portion; processing the medical image data to obtain a digital 3D model of the interest portion; extracting the data of the surface based on the digital 3D model of the interest portion; importing the digital 3D model of the interest portion into a software of reverse engineering and selecting a prosthesis model which is matching the surface of the digital 3D model of the interest portion; determining virtual positions which allow kirschner pins to enter into the digital 3D model of the interest portion and positions of bone cuts based on the prosthesis model and the digital 3D model of the interest portion; determining virtual locating positions based on the virtual positions; obtaining a digital 3D model of a customized surgical cutting guide based on the virtual locating positions, the positions of bone cuts and the data of the surface of the interest portion; and obtaining the customized surgical cutting guide through rapid prototyping technology from the digital 3D model.

Other objects, advantages and novel features of the present invention will become more apparent from the following detailed description when taken in conjunction with the accompanying drawings, in which:

DESCRIPTION OF PREFERRED EMBODIMENTS OF THE INVENTION

Reference is now made to the drawings to describe the invention in detail.

Figure 1:
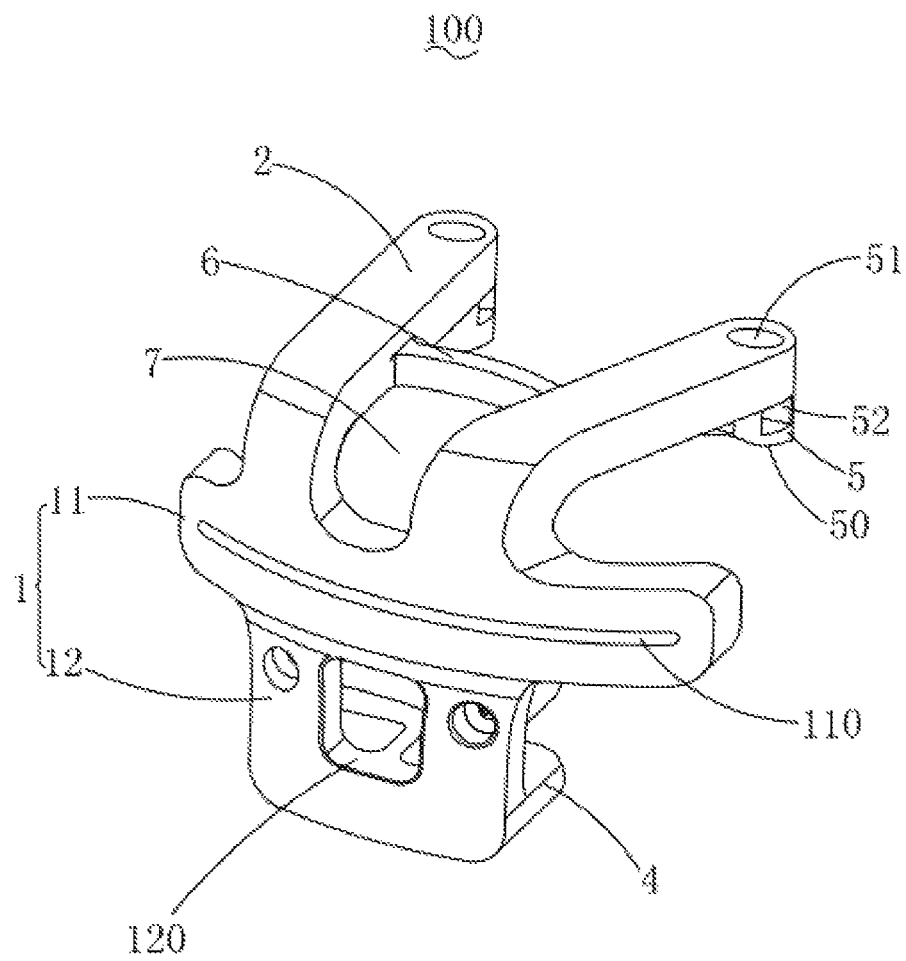
FIG. 1 is a perspective view of a customized surgical cutting guide used for surgical implantation of prosthetic knee component in TKR in accordance with a first preferred embodiment of the present invention.
Figure 2:
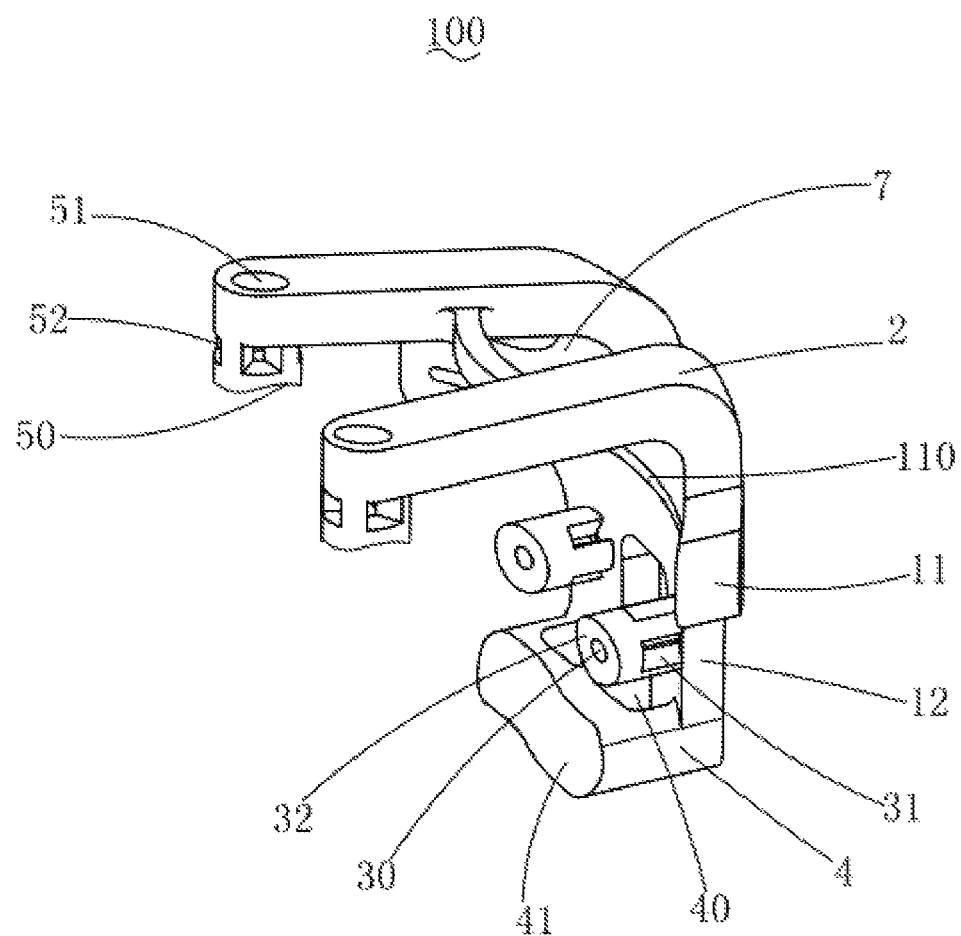
FIG. 2 is another perspective view of the customized surgical cutting guide shown in FIG. 1.
Figure 3:
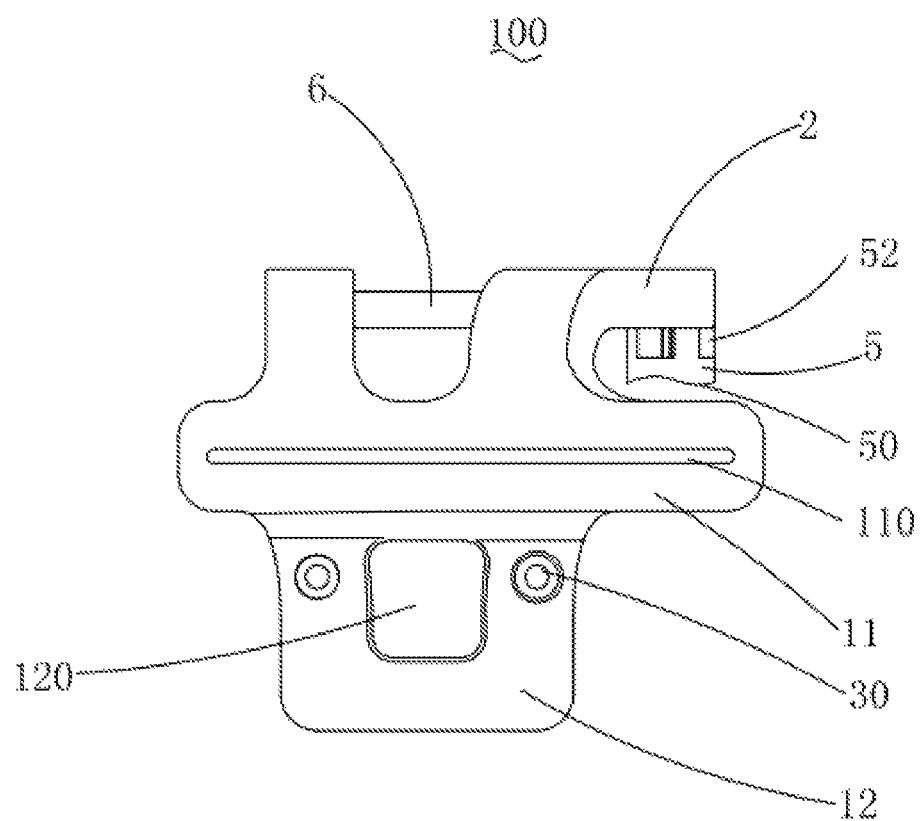
FIG. 3 is a front view of the customized surgical cutting guide shown in FIG. 1.
Figure 4:
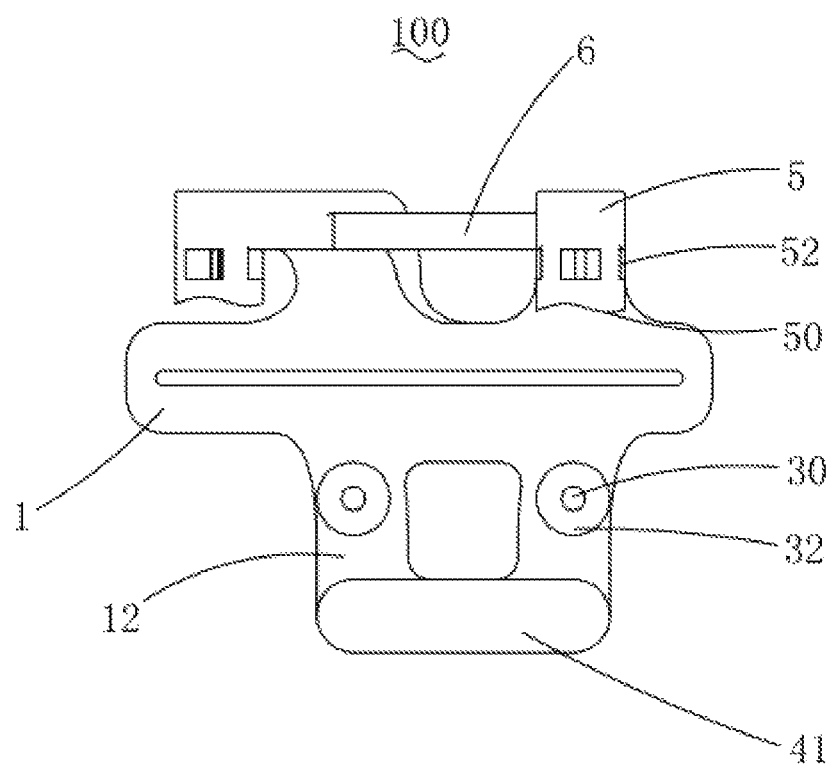
FIG. 4 is a back view of the customized surgical cutting guide shown in FIG. 1.
Figure 5:
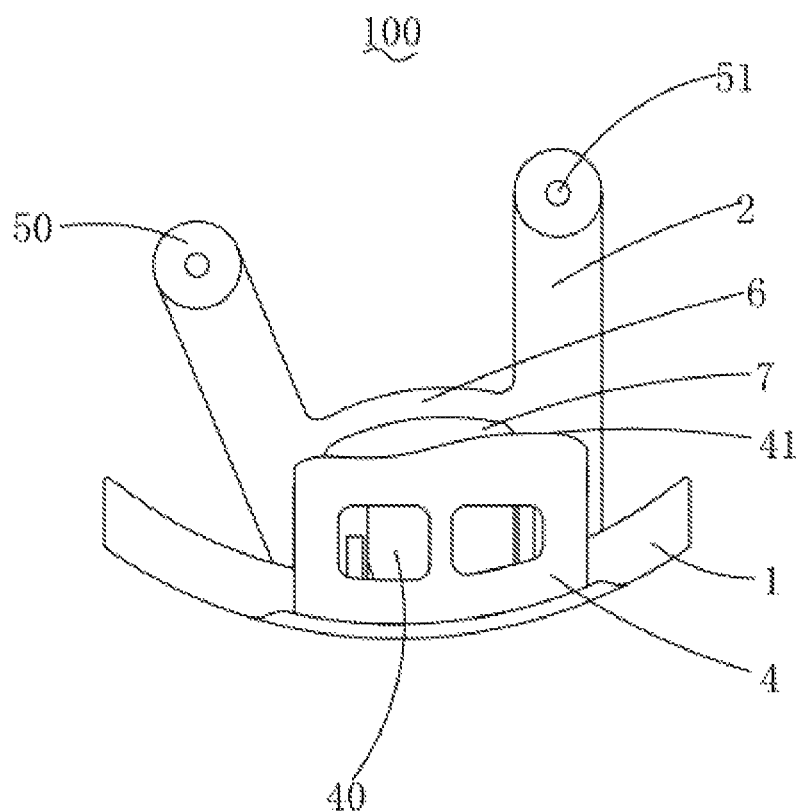
FIG. 5 is an upward view of the customized surgical cutting guide shown in FIG. 1
Figure 6:
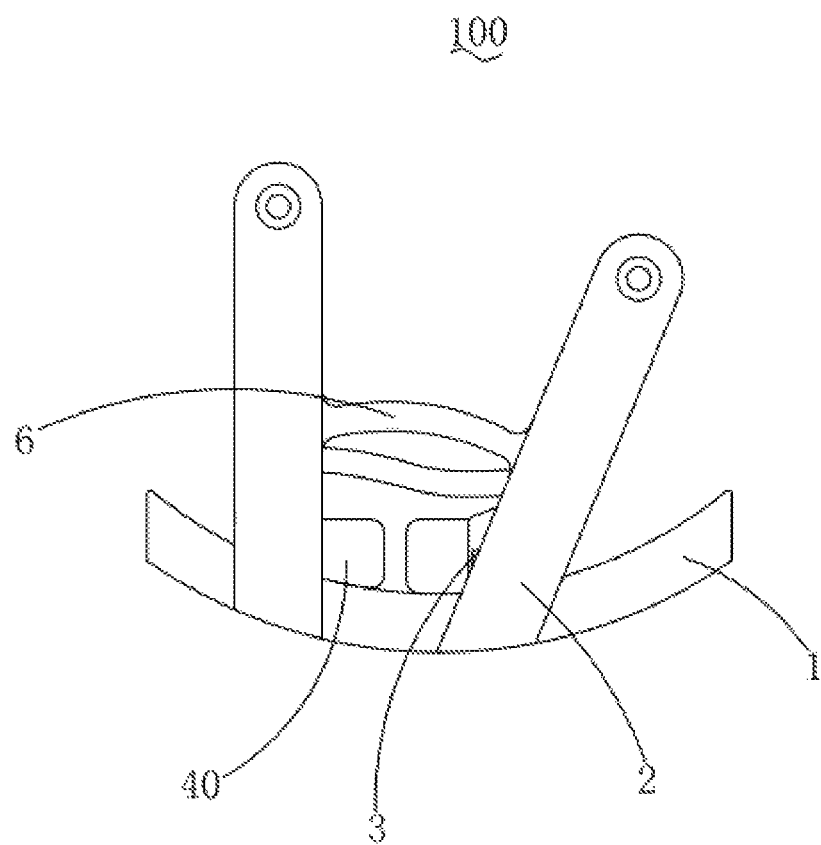
FIG. 6 is a top view of the customized surgical cutting guide shown in FIG. 1.
Figure 7:
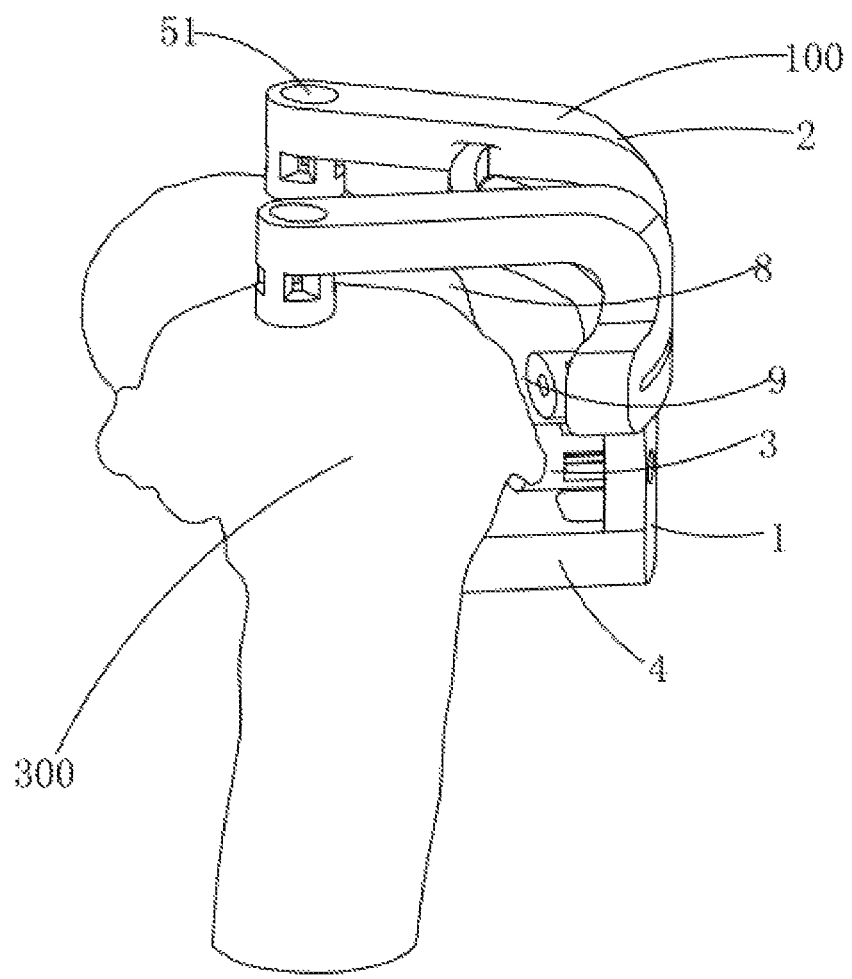
FIG. 7 is a perspective view of the customized surgical cutting guide assembled on a femur shown in FIG. 1.
Figure 8:
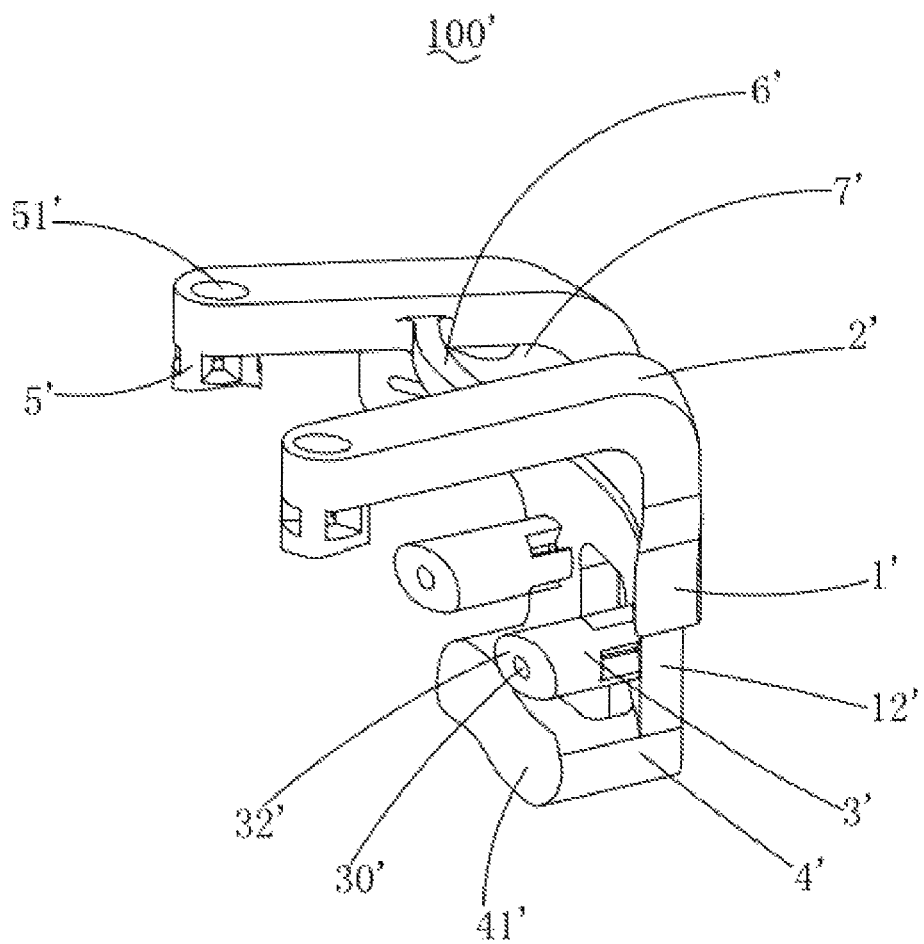
FIG. 8 is a perspective view of a customized surgical cutting guide in accordance with a second preferred embodiment of the present invention.
Figure 9:
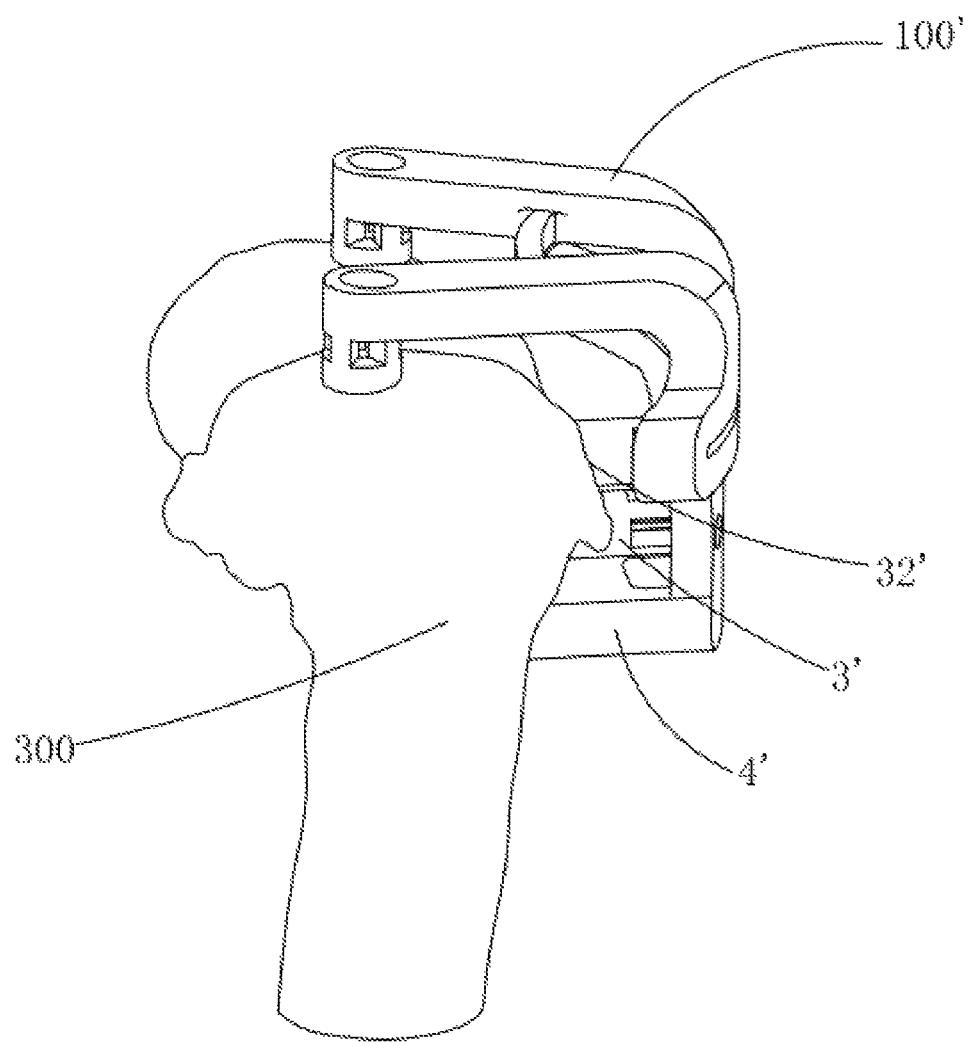
FIG. 9 is a perspective view of the customized surgical cutting guide assembled on a femur shown in FIG. 8.
Figure 10:
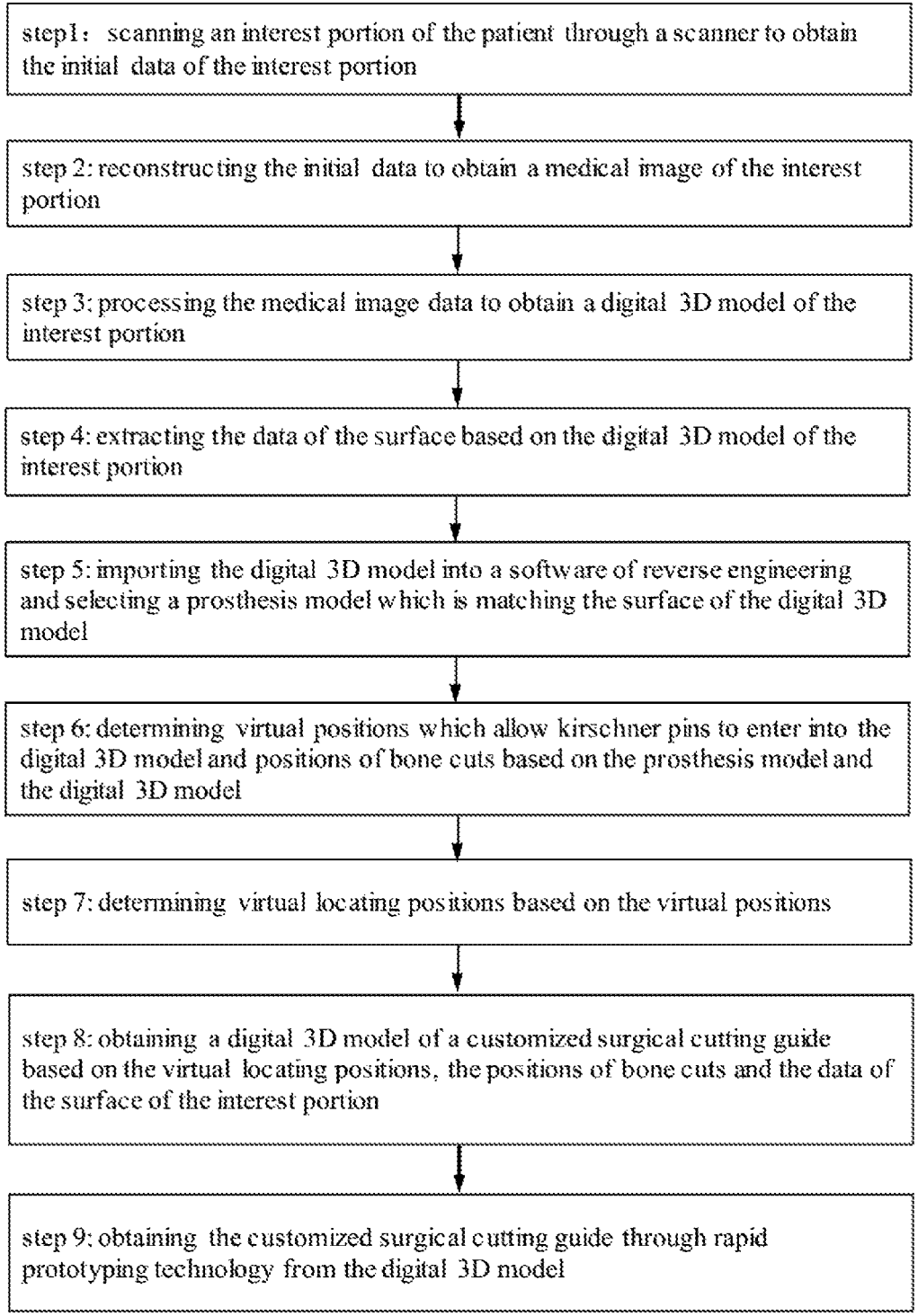
FIG. 10 is a flow chart of a method for making the customized surgical cutting guide in accordance with the preferred embodiment of the present invention.
Figure 11:
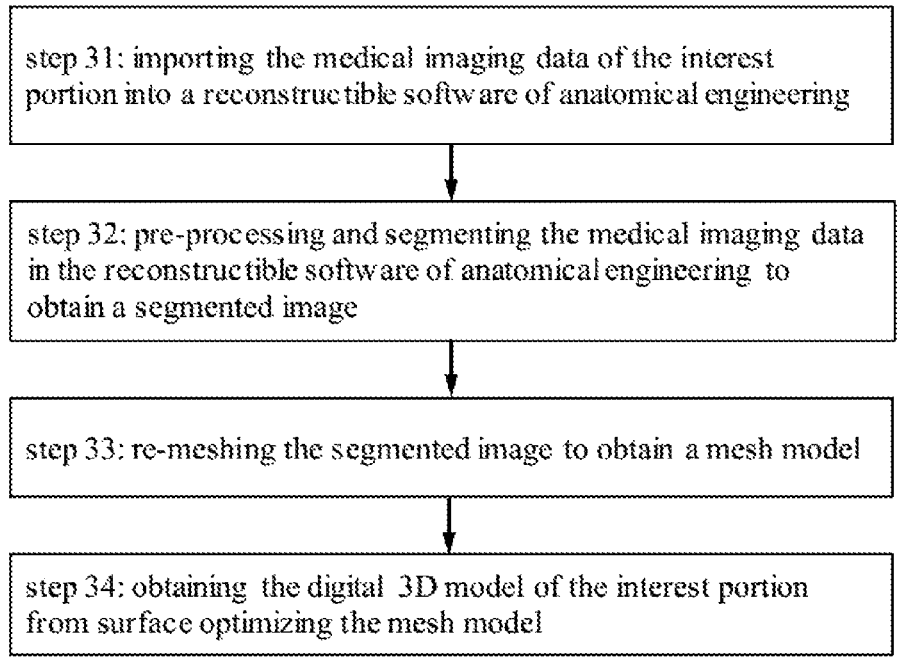
FIG. 11 is a flow chart of step 3 for making a 3D model of an interested portion shown in FIG. 10.
Figure 12:
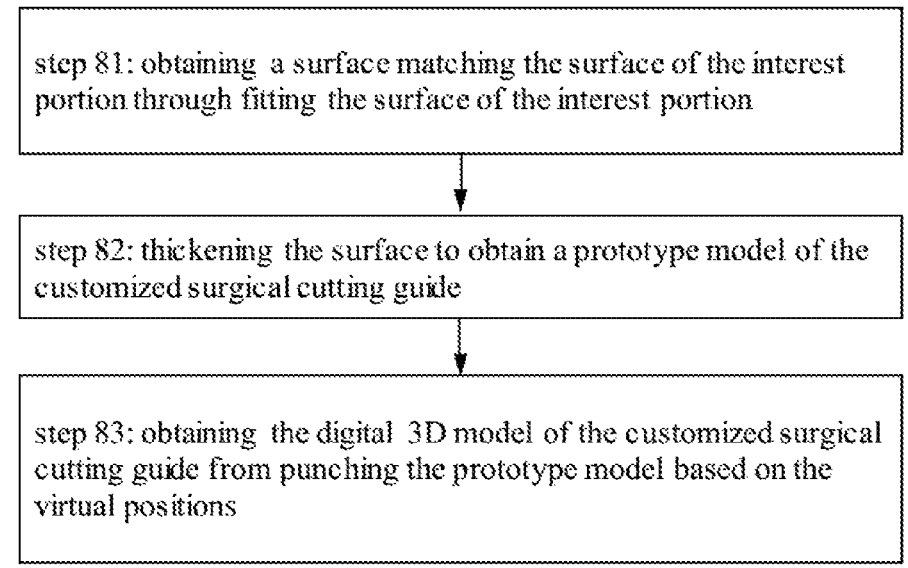
FIG. 12 is a flow chart of step 8 for making a 3D model of the customized surgical cutting guide shown in FIG. 10.

FIG. 1 to FIG. 7 illustrate a customized surgical cutting guide 100 used for surgical implantation of a prosthetic knee component in TKR in accordance with a first preferred embodiment of the present invention. FIG. 8 and FIG. 9 illustrate a customized surgical cutting guide 100' in accordance with a second preferred embodiment of the present invention. FIG. 10 to FIG. 12 describe a method for making the customized surgical cutting guide shown in FIG. 1 to FIG. 9.

Referring to FIG. 1 to FIG. 7, the customized surgical cutting guide 100 integrated through a rapid prototyping technology is positioned on a femur 300 to guide a surgeon to perform osteotomy. The customized surgical cutting guide 100 made of nylon by laser sintering includes a base 1 with an arc shape, a pair of arms 2 bending upwardly from a top of the base 1, a pair of cylinders 3 horizontally extending from a middle of the base 1, a convex portion 4 extending horizontally from a bottom of the base 1 and a pair of columns 5 each located at a tip of the corresponding arm 2. A reinforcing rib 6 configured with an arc shape is located between two arms 2 to prevent arms 2 from breakage caused by inadequate strength during the columns 5 attached to the corresponding portions of the femur 300. A window 7 is surrounded by the base 1, the arms 2 and the reinforcing rib 6 and is used for the surgeon to observe the fit between the customized surgical cutting guide 100 and the femur 300. The customized surgical cutting guide 100 can be also integrated by a stereo lithography apparatus.

The base 1 has a "T" shape and includes a main body 11 with an arc-strip shape and a basal-body 12 with a vertical and arc shape extending downwardly from the main body 11. The main body 11 defines a guiding slot 110 for allowing a surgical tool passing through and guiding the surgical tool to perform bone cuts. The guiding slot 110 configured with an arc shape extends transversely through the main body 11 along a thickness direction. The basal body 12 has an opening 120 located at a middle portion thereof for heat dissipation. The opening 120 has a square shape and is located at a portion below the guiding slot 110.

One arm 2 bends upwardly from a left side of the top of the base 1 and extends forwardly along a horizontal direction, and the other arm 2 bends upwardly from a right side of the top of the base 1 and extends forwardly along a horizontal direction. The arms 2 branch from the top of the main body 11 and extend away from each other in a horizontal direction. A distance formed between two arms is gradually increased. The arms 2, the cylinders 3 and the convex portion 4 are located at the same side of the base 1. A first gap 8 is defined between the arms 2 and the corresponding portion of the femur 300 after the customized surgical cutting guide 100 is mounted on the femur 300.

Two cylinder 3 each horizontally extends from a portion of the basal body 12 and are located at two opposite sides of the opening 120. Each cylinder 3 has a through hole 30 extending therethrough along a thickness direction thereof. The through hole 30 extends through the basal body 12 along an axis direction of the cylinder 3. The cylinder 3 defines a plurality of grooves 31 distributed along a circumferential direction thereof for heat dissipation during manufacturing. The grooves 31 each extends along a radial direction of the cylinder 3 to be connected with the through hole 30. The through hole 30 is a counter bore for Kirschner pin passing through. A second gap 9 is formed between the surface 32 of the cylinder 3 and the corresponding portion of the femur 300 after the customized surgical cutting guide 100 is positioned on the femur 300.

The convex portion 4 horizontally extends from a bottom portion of the basal body 12. The convex portion 4 and the cylinders 3 are located at the same side of the basal body 12. The convex portion 4 configured with a horizontal plate shape has a heat emission hole 40 vertically extending therethrough. The heat emission hole 40 has a square shape for heat dissipation during manufacture. The convex portion 4 has an abutting surface 41 with an irregular shapes for abutting against the corresponding surface of the femur 300 during the customized surgical cutting guide 100 is positioned on the femur 300. The convex portion 4 has a length protruding from the basal body 12 which is larger than that of the cylinder 3 protruding from the basal body 12. The cylinders 3 is suspended in midair during the convex portion 4 abuts against the femur 300.

Each column 5 extends downwardly from the tip portion of the corresponding arm 2 and contacts with a corresponding portion of the femur 300. Each column 5 has a contacting surface 50 contacting with the corresponding surface of the femur 300. The contacting surface 50 has an irregular shape. Each column 5 has a mounting hole 51 extending therethrough along an axial direction thereof for Kirschner pin passing through. Each column 5 defines a plurality of recesses 52 distributed thereon along a circumferential direction. Each recess 52 extends along a radial direction of the column 5 to connect with the mounting hole 51. The mounting hole 51 is located at a middle portion of the column 5 and extends through the corresponding arm 2. The mounting hole 51 is a counter bore and engages with the Kirschner pin to fasten the arms 2 of the customized surgical cutting guide 100 to the femur 300. The arms 2 are suspended in midair during the columns 5 abutting against the corresponding portions of the femur 300.

The customized surgical cutting guide 100 described in first preferred embodiment in accordance with the present invention is rapidly, accurately positioned on the femur 300 through the Kirschner pins passing through the mounting holes 51 of the columns 5 and the through holes 30 of the cylinders 3 into the femur 300 during the columns 5 and the convex portion 4 both abutting against the corresponding portions of the femur 300. So that misalignment of the customized surgical cutting guide 100 caused by bony spurs is avoided during full fit between the cutting guide and the femur. The deformation of the customized surgical cutting guide 100 caused by high temperature during manufacture is prevented by the opening 120 of the base 1 and the heat emission holes 40 of the convex portion 4. The customized surgical cutting guide 100 has a simple structure and integrated by laser sintering rapid prototype manufacturing.

FIG. 8 and FIG. 9 illustrate a customized surgical cutting guide 100' in second preferred embodiment in accordance with the present invention. The customized surgical cutting guide 100' includes a base 1', a pair of arms 2 branching from the top of the base 1', a pair of cylinders 3' horizontally extending from a middle of the base 1', a convex portion 4' extending horizontally from the bottom of the base 1', a pair of columns 5 each located at a tip of the corresponding arm 2 and a reinforcing rib 6 bridging between two arms 2. A window 7' is surrounded by the arms 2, the top of the base 1' and the reinforcing rib 6. The differences between the customized surgical cutting guide 100' illustrated in second embodiment and the customized surgical cutting guide 100 described in first embodiment are the length of the convex portion 4 protruding from the basal body 12 being equal to the length of the cylinders 3 protruding from the basal body 12 and the surfaces 32' of the cylinders 3' contacting with the corresponding portion of the femur during the convex portion 4' abutting against the femur. The surface 32' of the cylinder 3 has an irregular shape. The customized surgical cutting guide 100' is rapidly, accurately positioned on the femur 300 through the Kirschner pins passing through the through hole 30' and the mounting hole 51' of the columns 5 into the femur 300 during the cylinders 3, the convex portion 4 and the columns 5 all abutting against the femur 300.

FIG. 10 illustrates a method for manufacturing the customized surgical cutting guide 100, 100' described above. The method comprises following steps:

Step 1: scanning an interest portion of the patient through a scanner to obtain the initial data of the interest portion;

Step 2: reconstructing the initial data to obtain a medical image of the interest portion;

Step 3: processing the medical image data to obtain a digital 3D model of the interest portion;

Step 4: extracting the data of the surface based on the digital 3D model of the interest portion;

Step 5: importing the digital 3D model of the interest portion into a software of reverse engineering and selecting a prosthesis model which is matching the surface of the digital 3D model of the interest portion;

Step 6: determining virtual positions which allow kirschner pins to enter into the digital 3D model of the interest portion and positions of bone cuts based on the prosthesis model and the digital 3D model of the interest portion;

Step 7: determining virtual locating positions based on the virtual positions;

Step 8: obtaining a digital 3D model of a customized surgical cutting guide based on the virtual locating positions, the positions of bone cuts and the data of the surface of the interest portion;

Step 9: obtaining the customized surgical cutting guide through rapid prototyping technology from the digital 3D model.

Specifically, in step 1, the scanner is a computed tomography scanning equipment or a magnetic resonance imaging equipment. The medical imaging data is DICOM format data in step 3. The digital 3D model of the customized surgical cutting guide in step 9 is obtained by the computer-aided technology. The data of the digital 3D model are stored in STL format.

Referring to FIG. 11, a method for obtaining the digital 3D model of the interest portion in step 3 comprises following steps:

Step 31: importing the medical imaging data of the interest portion into a reconstructible software of anatomical engineering;

Step 32: pre-processing and segmenting the medical imaging data in the reconstructible software of anatomical engineering to obtain a segmented image;

Step 33: re-meshing the segmented image to obtain a mesh model;

Step 34: obtaining the digital 3D model of the interest portion from surface optimizing the mesh model.

The pre-processing of the medical imaging data in step 32 includes the de-noising of the image, or image enhancing, or image smoothing. The segmenting of the medical imaging data can be automatically segmentation or manual segmentation. The surface optimization in step 34 can be mesh refinement, or mesh smoothing, or mesh repairing, or mesh segmentation, or mesh shell.

The prosthesis model has holes allowing kirschner pins to pass through in step 5. The virtual positions are determined by the holes of the prosthesis model in step 6.

Referring to FIG. 12, a method of obtaining the digital 3D model of the customized surgical cutting guide in step 8 comprises the following steps:

Step 81: obtaining a surface matching the surface of the interest portion through fitting the surface of the interest portion;

Step 82: thickening the surface to obtain a prototype model of the customized surgical cutting guide;

Step 83: obtaining the digital 3D model of the customized surgical cutting guide from punching the prototype model based on the virtual positions.

The customized surgical cutting guide 100, 100' made by the method mentioned above is a customized cutting guide and can guide the surgeon to achieve accurately bone cuts. The customized surgical cutting guide is designed from the intraoperative prosthesis, so as to achieve good locating function for surgical implantation of prosthetic knee component in TKR.

Furthermore, although the present invention has been described with reference to particular embodiments, it is not to be construed as being limited thereto. Various alterations and modifications can be made to the embodiments without in any way departing from the scope or spirit of the present invention as defined in the appended claims.

What is claimed is:

1. A customized surgical cutting guide mounted on a femur for total knee replacement (TKR) comprising:
   a base having a plurality of cylinders located thereon;
   a pair of arms configured to branch from a top of the base, wherein at least one arm of the pair of arms has a column located at a tip thereof; and
   a convex portion configured to protrude from a bottom of the base and having an abutting surface with an irregular shape;
   wherein at least one of the plurality of cylinders has a through hole that is used for a krischnner pin passing through, and wherein the column has a contacting surface and has a mounting hole extending therethrough for positioning the at least one of the pair of arms, and wherein the at least one arm of the pair of arms, the at least one of the plurality of cylinders, and the convex portion are located at a same side of the base.

2. The customized surgical cutting guide of claim 1, wherein the through hole of the at least one of the plurality of cylinders extends along an axis direction of the cylinder corresponding to the at least one of the plurality of cylinders, and wherein the mounting hole of the at least one arm of the pair of arms extends along an axis direction of the column corresponding to the at least one arm of the pair of arms.

3. The customized surgical cutting guide of claim 2, wherein the column corresponding to the at least one arm of the pair of arms extends downwardly from the tip of the at least one arm of the pair of arms and has a contacting surface for matching a portion of the femur.

4. The customized surgical cutting guide of claim 3, wherein each column has a plurality of recesses surrounded thereof, and wherein at least one of the plurality of recesses extends along a radial direction of a corresponding column to connect with the mounting hole.

5. The customized surgical cutting guide of claim 2, wherein the cylinder has a plurality of grooves surrounded thereof, and wherein the grooves extend to connect with the through hole.

6. The customized surgical cutting guide of claim 1, wherein the convex portion defines an abutting surface for contacting with a corresponding portion of the femur, and wherein the convex portion has a plurality of heat emission holes extending vertically therethrough.

7. The customized surgical cutting guide of claim 6, wherein the pair of arms bend upwardly from the top of the base and extend away from each other in a horizontal direction, and wherein a distance formed between the pair of arms is gradually increased.

8. The customized surgical cutting guide of claim 7, wherein the base has a main body and a basal body, wherein the main body defines a slot configured with an arc shape extending along a thickness direction thereof, wherein the basal body has an opening extending therethrough, and wherein the opening is located bellow the slot, and wherein the plurality of cylinders are located at two opposite sides of the opening.

9. The customized surgical cutting guide of claim 8, wherein a length of at least one of the plurality of cylinders protruding from the basal body is smaller or equal to that of the convex portion protruding from the base.

10. The customized surgical cutting guide of claim 1, wherein a first gap is formed between the pair of arms.

11. The customized surgical cutting guide of claim 10, wherein a second gap is formed between at least one of the plurality of cylinders.

12. The customized surgical cutting guide of claim 1, wherein at least one of the plurality of cylinders has a surface with an irregular shape for contacting with the corresponding portion of the femur.

13. The customized surgical cutting guide of claim 1, wherein a reinforcing rib bridges the pair of arms, and wherein a window is surrounded by the pair of arms, the reinforcing rib and the base.

14. The customized surgical cutting guide of claim 1, wherein the customized surgical cutting guide is made by rapid prototyping technology.

15. A method for making the customized surgical cutting guide of claim 1, comprising:
    a) scanning an interest portion of a patient through a scanner to obtain an initial data of the interest portion;
    b) reconstructing the initial data to obtain a medical image of the interest portion;
    c) processing the medical image to obtain a digital three-dimensional (3D) model of the interest portion;
    d) extracting a data of the surface of the interest portion based on the digital 3D model of the interest portion;
    e) importing the digital 3D model of the interest portion into a software and selecting a prosthesis model which matches the surface of the digital 3D model of the interest portion;
    f) determining virtual positions which allow kirschner pins to enter into the digital 3D model of the interest portion and positions of bone cuts based on the prosthesis model and the digital 3D model of the interest portion;
    g) determining virtual locating positions based on the virtual positions;
    h) obtaining a digital 3D model of a customized surgical cutting guide based on the virtual locating positions, the positions of bone cuts and the data of the surface of the interest portion; and
    i) obtaining the customized surgical cutting guide through rapid prototyping technology from the digital 3D model of the customized surgical cutting guide.

16. The method of claim 15, wherein obtaining the digital 3D model of the interest portion comprises:
    a) importing the medical imaging data of the interest portion into a reconstructible software of anatomical engineering;
    b) pre-processing and segmenting the medical imaging data in the reconstructible software of anatomical engineering to obtain a segmented image;
    c) re-meshing the segmented image to obtain a mesh model; and
    d) obtaining the digital 3D model of the interest portion from surface optimizing the mesh model.

17. The method of claim 15, wherein obtaining the digital 3D model of the customized surgical cutting guide comprises:
    a) fitting the surface of the interest portion;
    b) thickening the fitted surface to obtain a prototype model of the customized surgical cutting guide; and
    c) obtaining the digital 3D model of the customized surgical cutting guide from punching the prototype model based on the virtual locating positions.

18. The method of claim 15, wherein the scanner is a computed tomography scanning equipment or a magnetic resonance imaging equipment, and wherein the digital 3D model of the customized surgical cutting guide is obtained by the computer-aided technology.

19. The method of claim 15, wherein the prosthesis model has holes allowing krischner pins to pass through.

20. The method of claim 19, wherein the virtual locating positions are determined by the holes of the prosthesis model.

* * * * *